(12) United States Patent
Timm

(10) Patent No.: US 8,186,511 B2
(45) Date of Patent: *May 29, 2012

(54) APPARATUS AND METHOD FOR RECONSTITUTING A PHARMACEUTICAL AND PREPARING THE RECONSTITUTED PHARMACEUTICAL FOR TRANSIENT APPLICATION

(75) Inventor: Edward J. Timm, St. Louis, MO (US)

(73) Assignee: Mobius Therapeutics, LLC, St. Louis, MO (US)

( * ) Notice: Subject to any disclaimer, the term of this patent is extended or adjusted under 35 U.S.C. 154(b) by 7 days.

This patent is subject to a terminal disclaimer.

(21) Appl. No.: 12/882,850

(22) Filed: Sep. 15, 2010

(65) Prior Publication Data
US 2011/0004170 A1   Jan. 6, 2011

Related U.S. Application Data

(63) Continuation of application No. 11/484,998, filed on Jul. 12, 2006, now Pat. No. 7,806,265.

(51) Int. Cl.
*A61B 19/02* (2006.01)
(52) U.S. Cl. ......... 206/438; 206/363; 206/570; 206/572
(58) Field of Classification Search .................. 206/363, 206/570, 571, 229, 438, 572; 604/290, 294, 604/411, 416
See application file for complete search history.

(56) References Cited

U.S. PATENT DOCUMENTS

| | | | |
|---|---|---|---|
| 3,650,393 A | 3/1972 | Reiss et al. | |
| 3,976,195 A | 8/1976 | Cohen | |
| 4,722,733 A | 2/1988 | Howson | |
| 4,842,577 A | 6/1989 | Konno et al. | |
| 4,871,352 A | 10/1989 | Tran | |
| 5,176,641 A | 1/1993 | Idriss | |
| 5,216,011 A | 6/1993 | Paborji et al. | |
| 5,324,258 A | 6/1994 | Rohrbough | |
| 5,336,188 A | 8/1994 | Kriesel | |
| 5,380,315 A * | 1/1995 | Isono et al. | 604/416 |
| 5,423,793 A * | 6/1995 | Isono et al. | 604/410 |
| 5,466,220 A * | 11/1995 | Brenneman | 604/87 |
| 5,558,874 A * | 9/1996 | Haber et al. | 424/402 |
| 5,566,828 A | 10/1996 | Claes et al. | |
| 5,628,729 A * | 5/1997 | Okabe | 604/20 |
| 5,830,187 A | 11/1998 | Kriesel et al. | |
| 5,860,806 A * | 1/1999 | Pranitis et al. | 433/80 |

(Continued)

OTHER PUBLICATIONS http://www.stevanatogroup.com/en/products-and-solutions/standard-vial-screw-neck.html.

(Continued)

*Primary Examiner* — Jacob K Ackun
*Assistant Examiner* — Jenine Pagan
(74) *Attorney, Agent, or Firm* — Thompson Coburn LLP

(57) ABSTRACT

An apparatus for preparing a pharmaceutical for transient application includes a tray having a sealed compartment, a vial of an ophthalmic formulation of mitomycin-C, a diluent carrier containing sterilized water, and a syringe that are all contained together in a single package. The component parts of the apparatus are used together to reconstitute the contents of the vial with the water in the diluent carrier, and then draw the reconstituted drug into the sealed compartment of the tray by a suction force produced by the syringe. In the tray compartment, the reconstituted drug is absorbed in an absorbent pad. The tray is opened to remove the pad and the absorbed drug from the tray compartment for use of the pad in transient application of the drug.

5 Claims, 5 Drawing Sheets

U.S. PATENT DOCUMENTS

| | | | |
|---|---|---|---|
| 5,891,084 | A | 4/1999 | Lee |
| 6,045,533 | A | 4/2000 | Kriesel et al. |
| 6,162,192 | A * | 12/2000 | Cragg et al. ............. 604/15 |
| 6,306,120 | B1 | 10/2001 | Tan |
| 6,355,024 | B1 | 3/2002 | Small et al. |
| 6,439,276 | B1 | 8/2002 | Wood et al. |
| 6,610,026 | B2 * | 8/2003 | Cragg et al. ............. 604/15 |
| 6,959,808 | B2 * | 11/2005 | Discko, Jr. ............. 206/229 |
| 2001/0022279 | A1 * | 9/2001 | Denyer et al. ............. 206/438 |
| 2001/0034509 | A1 | 10/2001 | Cragg et al. |
| 2002/0134373 | A1 * | 9/2002 | Gonda ............. 128/200.14 |
| 2003/0100921 | A1 * | 5/2003 | Addis et al. ............. 606/214 |
| 2003/0203856 | A1 * | 10/2003 | Rosazza et al. ............. 514/27 |
| 2005/0029150 | A1 * | 2/2005 | Hawkins ............. 206/524.8 |
| 2005/0137185 | A1 | 6/2005 | Lee et al. |
| 2005/0229931 | A1 * | 10/2005 | Denyer et al. ............. 128/204.23 |

OTHER PUBLICATIONS http://www.drugs.com/ppa/mitomycin.html.

Riccardo D'Eredita, Contact Diode Laser Myringotomy and Mitomycin C in Children, presented at the Annual Meeting of the American Academy of Otolaryngology-Head and Neck Surgery, Orlando, FL Sep. 21-24, 2003; 5 pages, Vicenza, Italy.

Peng Tee Khaw Article entitled "Trabeculectomy—the Moorfields Safe Surgery System" published in Textbook of Glaucoma Surgery; published by Mermond and Sharaway Dunitz, 2004.

* cited by examiner

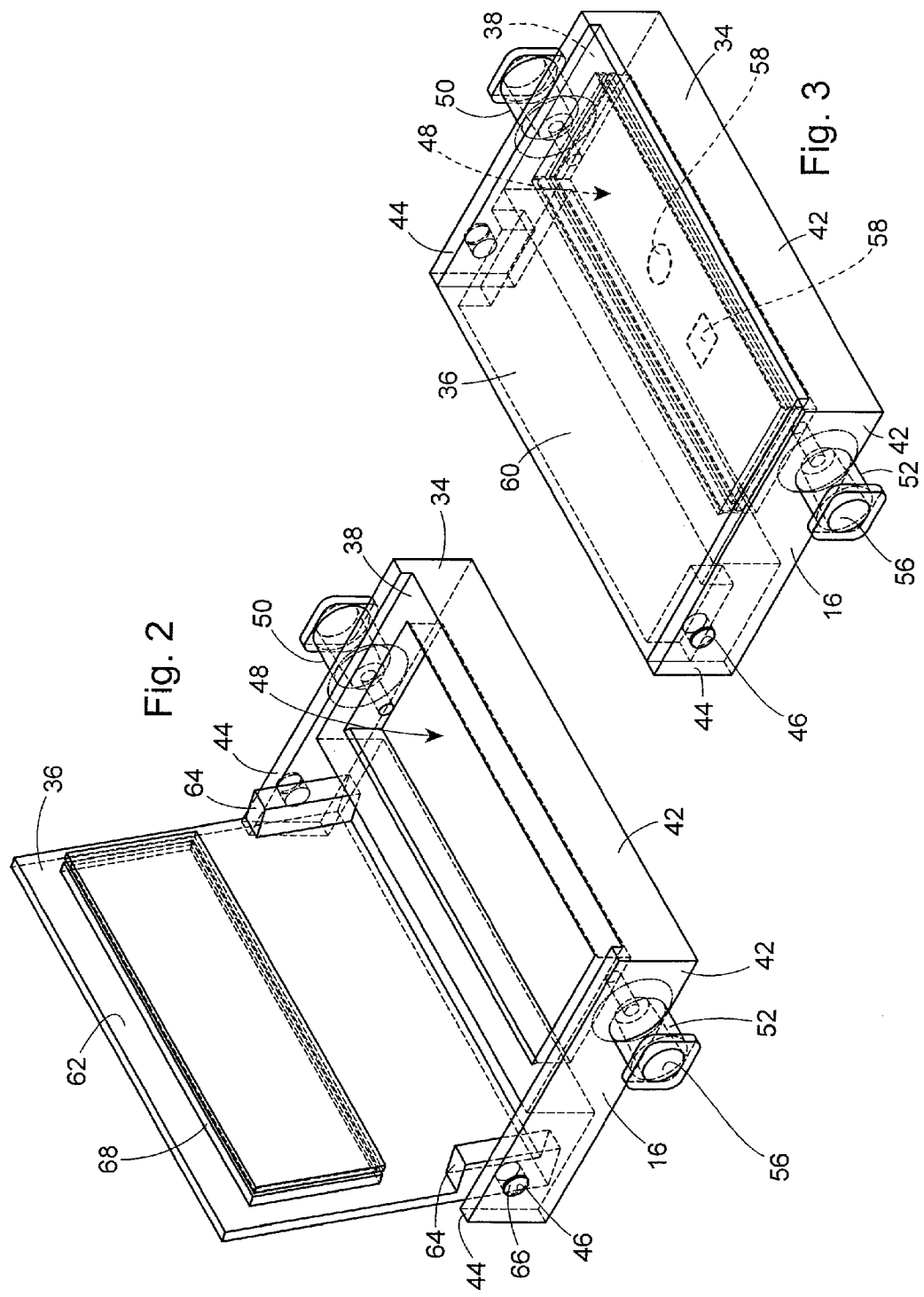

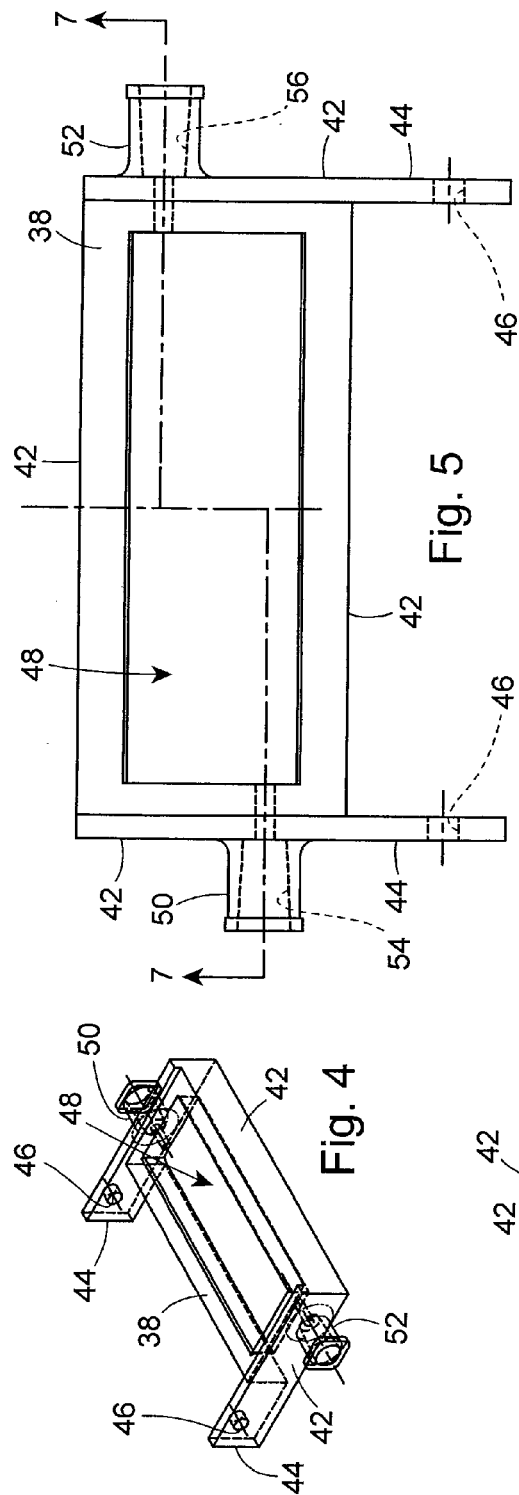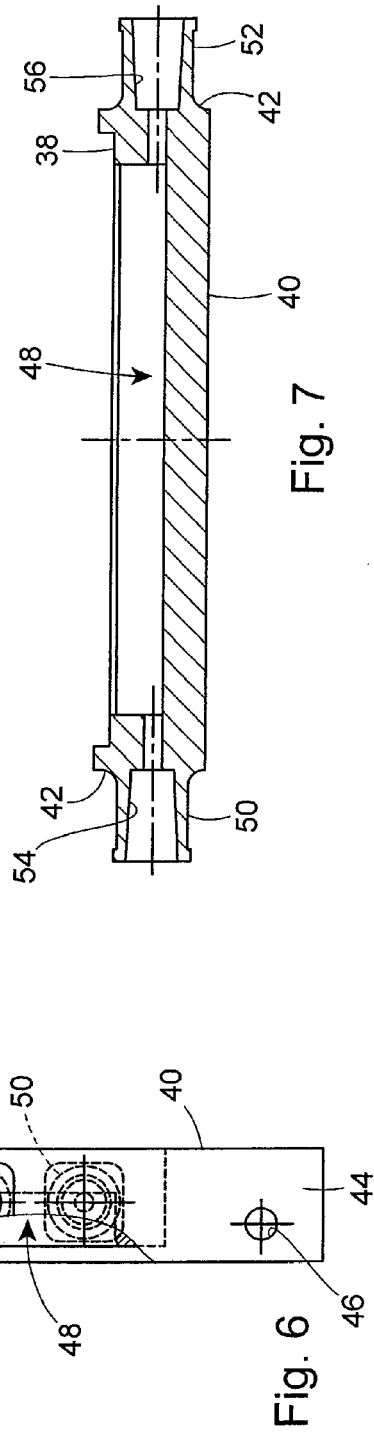

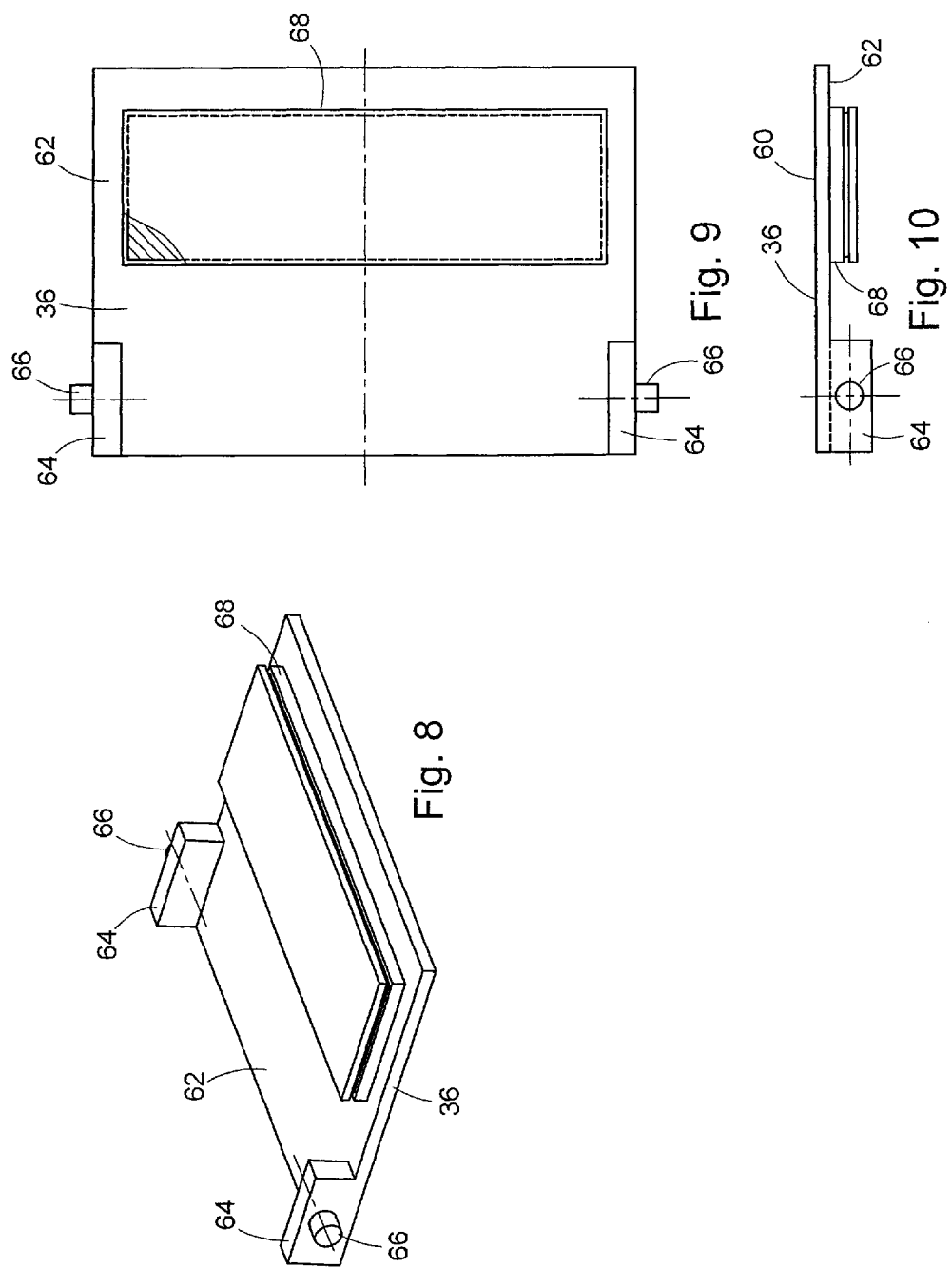

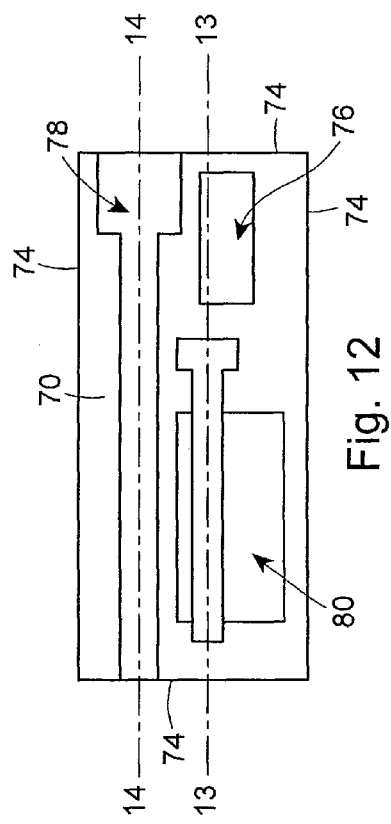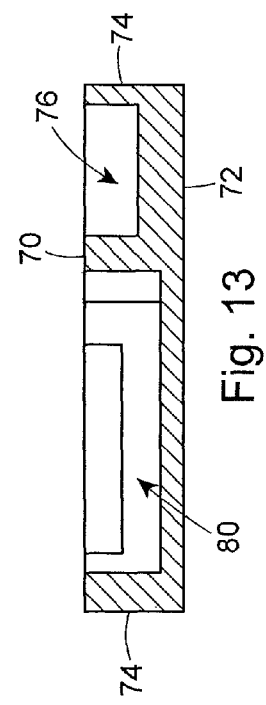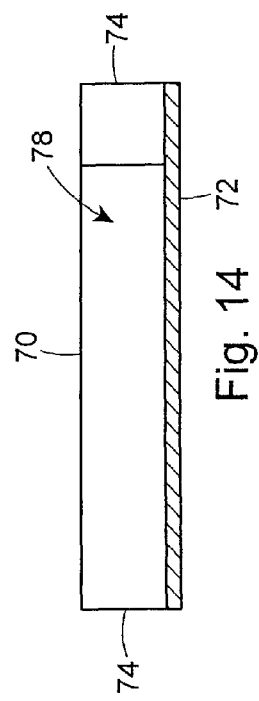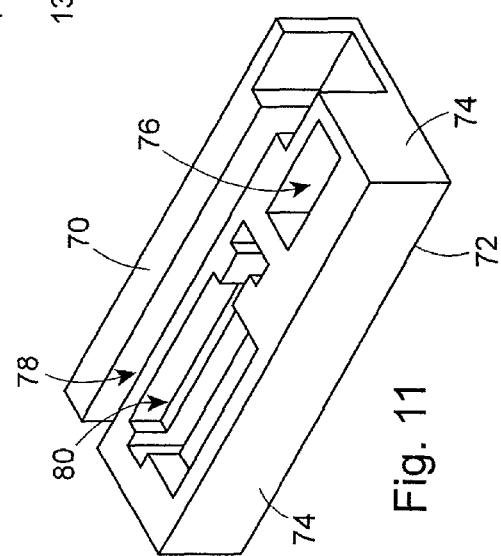

APPARATUS AND METHOD FOR RECONSTITUTING A PHARMACEUTICAL AND PREPARING THE RECONSTITUTED PHARMACEUTICAL FOR TRANSIENT APPLICATION

RELATED APPLICATIONS

This patent application is a continuation of patent application Ser. No. 11/484,998, which was filed on Jul. 12, 2006, and is currently pending.

BACKGROUND OF THE INVENTION (1) Field of the Invention

The present invention pertains to an apparatus and method for preparing a pharmaceutical for transient application. In particular, the present invention pertains to a tray having a sealed compartment, a vial of a single dose of an ophthalmic formulation of mitomycin-C, a diluent carrier containing sterilized water, and a syringe that are all contained together in a single package. The component parts of the apparatus are used together to reconstitute the contents of the vial with the water in the diluent carrier, and then draw the reconstituted drug into the sealed compartment of the tray by a suction force produced by the syringe. In the tray compartment, the reconstituted drug is absorbed in an array of absorbent pads. The tray is opened to remove the pad and absorbed drug from the tray compartment and for use of the pad in transient application of the drug.

(2) Description of the Related Art

Certain drugs that provide beneficial results when used to treat human diseases are dangerous to handle. An example of this type of drug is mitomycin-C. Mitomycin-C is primarily used as an anti-neoplastic agent in treating certain types of cancer. It has also been used in ophthalmology as a pterygium treatment and a glaucoma treatment. However, mitomycin-C is a chemotherapeutic agent and produces a toxic affect on cells. The drug is very dangerous, and chemotherapy precautions are used in the handling of the drug. What's more, once the drug is prepared, it is highly unstable, having a brief and finite shelf life. This makes it very difficult to use the drug in ophthalmologic procedures.

SUMMARY OF THE INVENTION

The present invention provides an apparatus and method that enables the safe and simplified preparation of a pharmaceutical such as mitomycin-C for transient application of the pharmaceutical. In the preferred embodiment of the invention, the apparatus of the invention is provided in a kit form with all component parts of the apparatus contained in a single package. The package provides a protective enclosure for the sterilized component parts prior to their use. The package also provides a mechanism for accounting for all of the component parts after their use to allow for the safe disposal of the used component parts.

The component parts include a vial of the pharmaceutical, in the preferred embodiment mitomycin-C, a syringe, a diluent carrier containing sterilized water, and a mixing tray.

The pharmaceutical vial, the syringe, and the diluent carrier of the apparatus have constructions that are known in the art. In the preferred embodiment of the invention, the vial is a typical vial containing a pharmaceutical, preferably mitomycin-C. The syringe has the typical construction of a syringe. The diluent carrier has the construction of any known diluent carrier of the prior art that contains sterilized water that is mixed with the pharmaceutical of the vial to reconstitute the pharmaceutical in the carrier. An example of such a carrier is the Smart-Rod™ type carrier of Duoject Medical Systems, Inc.

The tray of the apparatus has an interior compartment that is sealed closed by a cover of the apparatus. First and second passages in the tray communicate the sealed interior compartment with the exterior of the tray.

Each of the component parts is contained in the packaging of the invention which includes an interior resilient block that has cell cavities dimensioned to receive the vial, syringe, diluent carrier, and tray. The block is contained in a semi-rigid box dimensioned to receive the block, and the block and box are covered over by a sheet of packaging material that seals the sterilized component parts of the invention in the block inside the box of the packaging.

In use of the apparatus of the invention according to the method of the invention, the packaging is opened and the component parts are removed from the packaging. An array of pads of absorbent material are pre-positioned in the tray compartment interior. The vial of the pharmaceutical is connected to the diluent carrier and the pharmaceutical is mixed with the water in the carrier, reconstituting the pharmaceutical. The carrier is then connected to the first passageway of the tray, enabling communication of the reconstituted pharmaceutical from the carrier to the tray compartment interior. The syringe is connected to the second passageway of the tray. Withdrawing the plunger from the syringe creates a vacuum that exerts a suction force that is communicated through the tray second passageway, the compartment interior, and the tray first passageway to the interior of the diluent carrier. The reconstituted pharmaceutical in the diluent carrier is drawn by the suction force into the tray compartment interior where the reconstituted pharmaceutical is absorbed into the one or more absorbent pads contained in the tray compartment. The tray compartment can then be unsealed and opened, enabling the pad with the absorbed pharmaceutical to be removed from the tray compartment for transient application of the pharmaceutical to body tissue from the pad.

The apparatus of the invention and its method of use discussed above enable the safe and simplified reconstituting of a pharmaceutical such as mitomycin-C in preparing the pharmaceutical for transient application.

DESCRIPTION OF THE DRAWING FIGURES

Further features of the invention are set forth in the following detailed description of the preferred embodiment of the invention and in the application drawing figures.

FIG. 2 is a perspective view of the tray of the invention shown with a cover of the tray in an opened position.

FIG. 3 is a perspective view of the tray similar to that of FIG. 2, but with the cover shown in the closed position.

FIG. 4 is a perspective view of the tray similar to that of FIG. 3, but with the cover removed.

FIG. 5 is a top plan view of a tray.

FIG. 6 is an end elevation view of the tray shown partially in cross-section.

FIG. 7 is a cross-section view of the tray in the plane of the line 7-7 shown in FIG. 5.

FIG. 8 is a perspective view of the tray cover shown removed from the tray.

FIG. 9 is a plan view of the tray cover.

FIG. 10 is a side elevation view of the cover.

FIG. 11 is a perspective view of the resilient block of the packaging of the invention.

FIG. 12 is a top plan view of the block of FIG. 11.

FIG. 13 is a side sectioned view of the block of FIG. 11, in the plane of the line 13-13 shown in FIG. 12.

FIG. 14 is a side sectioned view of the block of FIG. 11, in the plane of the line 14-14 of FIG. 12.

DETAILED DESCRIPTION OF THE PREFERRED EMBODIMENT OF THE INVENTION

Figure 1:
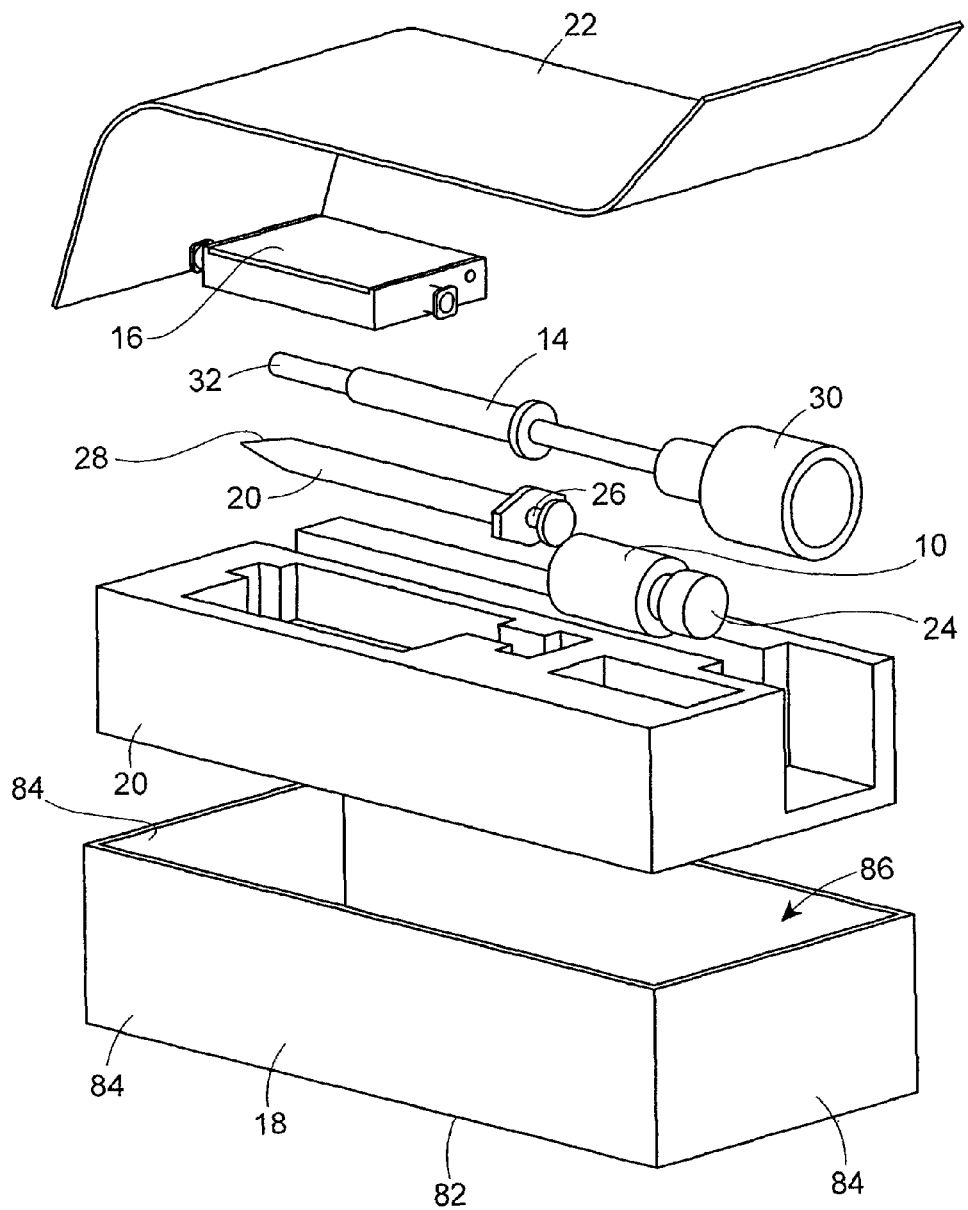
FIG. 1 is a perspective view of the component parts of the apparatus of the invention and of the packaging that combines the component parts as a kit in the packaging.

The component parts of the apparatus of the invention are shown in FIG. 1. These include the parts of the invention that enable the safe and simplified preparation of a pharmaceutical such as mitomycin-C for transient application of the pharmaceutical, and the parts that enable combining all of the component parts of the invention together in a kit that provides a protective enclosure for the sterilized component parts prior to their use, and also provides a mechanism for accounting for the component parts after their use and for their safe disposal. Several of the component parts are known in the prior art in one form or another. Therefore, these component parts will not be described in detail. The materials used to construct the component parts of the invention can be those typically used for similar apparatus.

The component parts include a vial 10 of the pharmaceutical, a syringe 12, a diluent carrier 14, a mixing tray 16, a semi-rigid packaging box 18, a resilient packaging block 20, and a sheet of packaging material 22. As stated earlier, each of these component parts can be constructed of the materials typically used to manufacture similar parts.

The pharmaceutical vial 10 has a construction that is known in the art. In the preferred embodiment, the pharmaceutical contained by the vial 10 is a single dose of an ophthalmic formulation of mitomycin-C. Like conventional pharmaceutical vials, the vial 10 has a top 24 that can be pierced by a syringe needle which seals closed after the needle is removed from the top 24.

The syringe 12 also has the typical construction of a syringe. In the preferred embodiment of the invention, the syringe 12 is a one cc syringe. The syringe 12 has a plunger 26 that is manually withdrawn from the body of the syringe to produce a suction force at the distal tip 28 of the syringe.

The diluent carrier 14 also has the construction of any known diluent carrier. In the preferred embodiment, the diluent carrier 14 has an interior bore that contains sterilized water. The amount of water is provided to mix with the pharmaceutical contained by the vial 10 to reconstitute the pharmaceutical in the carrier 14. The carrier 14 has a proximal end 30 that is adapted to receive the vial top 24. A needle (not shown) is positioned in the carrier proximal end 30 to pierce the vial top 24 and communicate the pharmaceutical contained by the vial 10 with the water contained in the carrier 14. The carrier distal end 32 is adapted to discharge the pharmaceutical reconstituted with the water from the interior of the carrier 14. As stated earlier, reconstituting carriers of this type are known in the art. An example of such a carrier is the Smart-Rod™ type carrier of Duoject Medical Systems, Inc.

The tray 16 of the apparatus has a novel construction that enables the safe and simplified preparation of a pharmaceutical such as mitomycin-C for transient application of the pharmaceutical. Referring to drawing FIGS. 2-10, the tray is basically comprised of a tray body 34 and a tray cover 36. Preferably the materials of the body 34 and cover 36 are plastic materials that may be employed in containing a pharmaceutical such as mitomycin-C.

The tray body 34 has a rectangular block configuration with opposite top 38 and bottom 40 exterior surfaces, and a plurality of side 42 exterior surfaces. A pair of arms 44 protect outwardly from one of the tray side surfaces 42. The arms 44 have axially aligned post holes 46 that function as pivot connections for the cover 36.

A cavity 48 is recessed into the top surface 38 of the tray. As shown in the drawing figures, the cavity 48 has a rectangular configuration and defines an interior compartment having an interior volume between the tray top 38 and bottom 40 surfaces, and the tray side surfaces 42. The interior volume of the compartment 48 is accessible through the top opening of the cavity in the tray top surface 38.

A pair of first 50 and second 52 cylindrical connectors project outwardly from opposite side surfaces 42 of the tray 34. The first connector 50 has a first interior passage 54 that extends through the connector 50 and through the tray 34. The first passage 54 communicates the exterior environment of the tray with the tray compartment 48. The second connector 52 has a second interior passage 56 that extends through the connector and the tray 34. The second passage 56 also communicates the exterior environment of the tray with the tray compartment 48. The first passage 54 and the second passage 56 are separate from each other and are separate from the top opening of the compartment 48.

The tray compartment 48 has an interior volume that is dimensioned to receive and accommodate one or more absorbent pads 58 in the compartment. The pads 58 are represented by the dashed lines in FIG. 3. In the preferred embodiment, the pads 58 are constructed of an absorbent material that is known in the art and is used for the transient application of a pharmaceutical such as mitomycin-C. An example of such a pad is a Weck-cel™ type surgical sponge provided by Medtronic Xomed, Inc.

The cover 36 has a planar rectangular configuration that is dimensioned to fit over the tray top surface 38 as shown in the drawing figures. The cover 36 has a top surface 60 and an opposite bottom surface 62. A pair of support blocks 64 project outwardly from the cover bottom surface 62. The blocks 64 support a pair of pivot posts 66 that engage in the tray post holes 46 to provide a pivoting connection between the cover 36 and the tray 34. The pivot posts 66 enable the cover to be moved between an opened position where the cover 36 is displaced from the tray top surface 38 as shown in FIG. 2, and a closed position where the cover 36 is positioned over the tray top surface 38 as shown in FIG. 3. Other equivalent means of moving the cover 36 relative to the tray 34 between opened and closed positions such as those shown in FIGS. 2 and 3 may also be employed. For example, the cover 36 could be completely removable from the tray 34 in the opened position of the cover.

The cover 36 is also provided with a sealing projection 68 on the cover bottom surface 62. The sealing projection 68 has a rectangular configuration that is complementary to the rectangular configuration of the top opening of the tray compartment 48. The projection 68 is dimensioned to fit in a sealing engagement in the top opening of the tray compartment 48 when the cover is moved to the closed position shown in FIG. 3. The projection 68 extends into the tray compartment 48, but does not occupy the entire interior volume of the compartment. This provides ample room for one or more of the absorbent material pads 58 in the tray compartment when the cover is moved to the closed position.

Each of the above-described component parts of the apparatus is contained in the packaging of the apparatus that includes the box 18, the resilient block 20, and the sheet of packaging material 22. As stated earlier, each of these packaging component parts is constructed of materials used in the safe storage, transport, and disposal of pharmaceuticals and instruments used with pharmaceuticals such as mitomycin-C.

The block 20 is constructed of a resilient material such as foam rubber. The block 20 has a top surface 70 and an opposite bottom surface 72, and four surrounding side surfaces 74. A vial cell cavity 76 is formed in the block top surface 70. The vial cell cavity 76 is dimensioned to receive the vial 10 in a snug friction fit in the cavity. A carrier cell cavity 78 is also formed into the block top surface 70. The carrier cell cavity 78 is dimensioned to receive the diluent carrier 14 in a snug secure fit in the cavity. A syringe and tray cell cavity 80 is also formed in the block top surface 70. The syringe and cell cavity 80 is dimensioned to first receive the syringe 12 in a snug secure fit in the bottom of the cavity, and then receive the tray 16 in a snug secure fit in the top of the cavity over the syringe. The cell cavities of the block 20 securely hold the component parts of the apparatus described above and provide cushioning of the component parts to protect the parts during their storage and transportation.

The box 18 is constructed with a bottom 82 and four side walls 84 that define an interior volume 86 of the box. The interior volume 86 is dimensioned to receive the resilient block 20 and securely hold the resilient block 20 in the box interior. The top edges of the box side walls 84 are positioned in substantially the same plane as the top surface 70 of the resilient block 20.

The sheet of packaging material 22 can be any type of material currently used to provide a sealed enclosure of the box 18, the resilient block 20, and the vial 10, syringe 12, diluent carrier 14, and tray 16 contained in the block 20. The packaging material 22 can be shrink-wrap applied around the component parts of the invention, or can be resealable packaging material that can be resealed after the component parts have been removed from the packaging and used.

In use of the apparatus of the invention according to the method of the invention, the packaging is first opened by removing the sheet material 22 from the box 18 and block 20. The vial 10, syringe 12, diluent carrier 14, and tray 16 are removed from their respective cell cavities in the resilient block 20.

The sealed cover 36 is moved to its opened position relative to the tray body 34, providing access into the tray compartment 48. One or more absorbent pads 58 are positioned in the tray compartment 48. The cover 36 is then moved to the closed position on the tray 34, sealing the pads 58 in the compartment 48.

The vial 10 of pharmaceutical, preferably mitomycin-C, is then connected to the diluent carrier proximal end 30. This communicates the pharmaceutical in the vial 10 with the interior bore of the carrier 14. The pharmaceutical mixes with the water in the carrier 14, reconstituting the pharmaceutical. The carrier distal end 34 is then connected to the first connector 50 of the tray 34. This communicates the reconstituted pharmaceutical in the interior bore of the carrier 14, through the first passage 54, with the compartment 48 of the tray 34.

The syringe 12 is next connected to the tray 34. The syringe distal end 28 is connected to the tray second connector 52 with the syringe interior communicating through the second passage 56 with the interior volume of the tray compartment 48.

Withdrawing the plunger 26 from the syringe 12 creates a suction vacuum force at the syringe distal end 28. The suction force is communicated through the second passage 56 with the interior volume of the tray compartment 48, and then through the first passage 54 with the interior bore of the diluent carrier 14. The reconstituted pharmaceutical in the diluent carrier 14 is drawn by the suction force through the first passage 54 and into the interior volume of the tray compartment 48. In the compartment 48, the reconstituted pharmaceutical is absorbed into one or more of the pads 58.

The cover 36 is then moved to its opened position relative to the tray body 34, providing access to the interior volume of the compartment 48 through the top opening of the compartment. The pads 58 with the absorbed pharmaceutical can then be removed from the compartment 48 for transient application of the pharmaceutical to body tissue from the pad.

The apparatus of the invention and its method of use discussed above enable the safe and simplified reconstituting of a pharmaceutical such as mitomycin-C and the transient application of the reconstituted pharmaceutical. Although the apparatus and its method of use have been described above by referring to a single embodiment of the invention, it should be understood that modifications and variations could be made to the apparatus of the invention and its method of use without departing from the intended scope of the application claims.

The invention claimed is:

1. An apparatus for reconstituting a pharmaceutical for transient application, the apparatus comprising:
    a pharmaceutical container containing a pharmaceutical in a condition to be reconstituted;
    a diluent carrier containing an amount of sterile water, the diluent carrier being configured and adapted to be operatively connected to the pharmaceutical container in a manner such that the sterile water can mix with, and thereby reconstitute, the pharmaceutical;
    a sterile syringe;
    a tray having an interior compartment, the interior compartment of the tray containing at least one pad of absorbent material, the tray having a first passageway that is configured and adapted to operatively connect to the diluent carrier in a manner such that at least some of the reconstituted pharmaceutical can be transferred into the interior compartment of the tray where it can be absorbed by the pad of absorbent material, the tray also having an access opening and a cover, the access opening being configured and adapted to allow the pad of absorbent material to be removed from the interior compartment of the tray, the cover being movable relative to the access opening in a manner such that cover can selectively open and close the access opening, the tray having a second passageway, the second passageway being adapted and configured to be operatively connected to the syringe in a manner such that at least some of the reconstituted pharmaceutical can be transferred from the interior compartment of the tray into the syringe, the tray and the pad of absorbent material being sterile;
    a packaging container, the packing container comprising an internal volume that is sealed, the internal volume housing the diluent carrier, the pharmaceutical container, the syringe, and the tray in a sterile environment.

2. An apparatus in accordance with claim 1 wherein the cover is pivotally connected to the remainder of the tray such that the cover remains attached to the tray when the cover opens the access opening of the tray.

3. An apparatus in accordance with claim 1 wherein the pharmaceutical is a chemotherapeutic agent.

4. An apparatus in accordance with claim 1 wherein the pharmaceutical is mitomycin-C.

5. An apparatus in accordance with claim 1 wherein the internal volume of the packaging container comprises non-contiguous regions.

* * * * *